(12) United States Patent
Holcomb et al.

(10) Patent No.: US 7,205,045 B2
(45) Date of Patent: Apr. 17, 2007

(54) DEVICES FOR CALIBRATING OPTICAL SCANNERS AND METHODS OF USING THE SAME

(75) Inventors: Nelson R. Holcomb, San Jose, CA (US); Russell A. Parker, San Jose, CA (US); Steven M. Lefkowitz, Branford, CT (US)

(73) Assignee: Agilent Technologies, Inc., Santa Clara, CA (US)

( * ) Notice: Subject to any disclaimer, the term of this patent is extended or adjusted under 35 U.S.C. 154(b) by 422 days.

(21) Appl. No.: 10/944,457

(22) Filed: Sep. 16, 2004

(65) Prior Publication Data

US 2005/0137280 A1   Jun. 23, 2005

(51) Int. Cl.
*G11B 11/105* (2006.01)

(52) U.S. Cl. .......................... 428/332; 428/338; 522/1; 523/137; 524/86; 528/480

(58) Field of Classification Search ................ 428/332, 428/338; 522/1; 523/137; 524/86; 528/480
See application file for complete search history.

(56) References Cited

U.S. PATENT DOCUMENTS

| 4,087,672 A | 5/1978 | Yi |
| 4,545,018 A | 10/1985 | Clements et al. |
| 4,825,034 A | 4/1989 | Auvert et al. |
| 4,866,243 A | 9/1989 | Sakane et al. |
| 4,868,126 A | 9/1989 | Schwartz |
| 4,918,611 A | 4/1990 | Shyu et al. |
| 5,040,047 A | 8/1991 | Cole et al. |
| 5,211,805 A | 5/1993 | Srinivasan |
| 5,464,960 A | 11/1995 | Hall et al. |
| 5,585,639 A | 12/1996 | Dorsel et al. |
| 5,631,734 A | 5/1997 | Stern et al. |
| 5,772,656 A | 6/1998 | Klopotek et al. |
| 5,922,612 A | 7/1999 | Alder et al. |
| 5,981,956 A | 11/1999 | Sten et al. |
| 6,259,524 B1 | 7/2001 | Hofstraat et al. |

FOREIGN PATENT DOCUMENTS

| EP | 0050159 B1 | 8/1986 |
| EP | 0557719 B1 | 8/1995 |
| WO | WO98/49537 | 11/1998 |
| WO | WO01/59503 | 8/2001 |

*Primary Examiner*—Bernard Lipman

(57) ABSTRACT

Calibration devices for optical scanners and methods for their use are provided. The subject devices are characterized by having a polymeric coating with at least one fluorescent agent, where the devices have minimal local and global nonuniformities. The subject device may also include one or more photobleached regions. In using the subject devices, a surface is illuminated with at least one light source, fluorescence data is obtained from the surface and the optical system is calibrated based upon the obtained fluorescence data. The subject invention finds use in a variety of optical scanners, including biopolymeric array optical scanners. Also provided are kits for use in verifying and calibrating optical scanners.

42 Claims, 2 Drawing Sheets

DEVICES FOR CALIBRATING OPTICAL SCANNERS AND METHODS OF USING THE SAME

This application claims priority to application Ser. No. 10/008,598, filed Dec. 4, 2001, under 35 U.S.C. 120, now U.S. Pat. No. 6,794,424, the entirety of which is incorporated herein by reference.

FIELD OF THE INVENTION

The field of this invention is calibration devices for optical scanning devices and more particularly devices for use in calibrating an optical scanning device used to scan arrays having fluorescent sample regions thereon.

BACKGROUND OF THE INVENTION

"Biochips" or arrays (also known as microarrays) of binding agents, such as oligonucleotides, cDNA and peptides, and the like have become an increasingly important tool in the biotechnology industry and related fields. These binding agent arrays, in which a plurality of binding agents are deposited onto a solid support surface in the form of an array or pattern, find use in a variety of applications, including gene expression analysis, drug screening, nucleic acid sequencing, mutation analysis, and the like.

In array-based assays in which an array of binding agents is employed, the array surface is reacted with one or more analytes, such as polynucleotide analytes, receptor proteins or antiligand molecules, under conditions that promote specific, high-affinity binding of the analyte molecules to one or more of the array members. Typically, the goal is to identify one or more position-addressable members of the library array which bind to the analyte, as a method of screening for array compounds which bind the analyte. Typically, the analyte is labeled with a detectable reporter such as a fluorescent agent, which in effect can fluorescently label the one or more array regions where analyte binding to the array has occurred.

Once the binding of the analyte to one or more array members has occurred, the arrays are read, usually by optical means, where a variety of optical scanning devices have been proposed for reading such arrays (see for example U.S. Pat. Nos. 5,324,633 and 5,585,639, the disclosures of which are herein incorporated by reference). The optical means included in these array scanning devices typically includes a light source, e.g., a laser, photodiode or the like, for transmitting light onto the array and a detector, e.g., a photomultiplier or the like, for detecting a parameter of the transmitted light, e.g., light absorption, fluorescence, etc. Typically, a microprocessor working under the control of a software program is associated with the device, which microprocessor processes the information received by the detector, for example it performs calculations, comparisons and the like.

As will be apparent, it is imperative that the optical means in these scanners performs consistently over time. In other words, it is important that the light source and detector accurately and precisely detect fluorescently labeled regions on an array surface and that such detection is consistent amongst scanners. Thus, it would be advantageous if array optical scanners could be periodically calibrated to achieve and maintain such consistency, precision, accuracy, etc., and also to ensure that variations between optical scanners are minimized, i.e., each optical scanner produces substantially the same results as any other scanner. More precisely, it would be advantageous if the optical components of the scanner, e.g., the light source and/or light detector and certain other optical components of the system including the scanning lens(es), optical stage and the scanner mirror(s), were periodically checked and, if necessary, re-adjusted.

Typically, the optical means of a scanner are calibrated during manufacture. Methods and devices are known for calibrating light sources (see for example U.S. Pat. Nos. 5,464,960 and 5,772,656). However, few are known for calibrating optical components, such as an optical detector for example, after manufacture. Thus, optical detectors and various other optical components are usually not calibrated periodically, due to the lack of an easy, precise and inexpensive end-user calibration tool. However, one method that has been developed to calibrate optical detectors of scanners after manufacture uses a substrate having a pattern of reflective metal, typically chromium, thereon. The method relies solely on the reflection of light from the chromium pattern, where such reflective light measurements are used to calibrate the optical detector of the scanner. One disadvantage with this system is that although it is capable of calibrating the scanner's positioning mechanism with high precision, it lacks the capability to detect power changes in the laser or reduced responses in the detector. Another disadvantage associated with this method is that it is wavelength insensitive. In other words, using reflectance to calibrate the optical detector of an optical scanner that is intended to scan fluorescently labeled probes, does not evaluate the optical detector of the scanner in regards to the wavelength of light that will ultimately be emitted, e.g., fluorescence, when an actual array is scanned by the optical scanner. Another significant disadvantage is that the chromium tool does not include a means to subtract background signal from the reflectance data, aside from the dark current typical of all detectors, and thus the reflectance data may be over or under estimated which may then skew the calibration of the optics.

To be a suitable reference, the reference should provide a stable output, preferably over a significant period of time, should have minimal local and global nonuniformities, should not be substantially degraded by the optics of the scanner, should also produce a stable output at the frequency or wavelength range of interest, i.e., corresponding to a wavelength/frequency emitted from an actual scanned array (e.g., emitted from fluorescently labeled probes) and a means to measure and subtract background signal. As such, there is continued interest in the development of new devices for optical scanner calibration devices and methods of using the same. Of particular interest would be the development of an array optical scanner calibration device, and methods of use thereof, that produces a stable output at the frequency or wavelength of interest, has minimal local and global nonuniformities, and is easy to manufacture and use.

Relevant Literature

U.S. Patent documents of interest include U.S. Pat. Nos. 4,868,105; 5,124,246; 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,563,034; 5,585,639; 5,599,695; 5,624,711; 5,631,734; 5,639,603; 5,658,734; 5,681,702; and 5,981,956. Other documents of interest include WO 93/17126; WO 95/11995; WO 95/35505; WO 97/14706 and WO 98/30575; WO 98/24933; EP 742287; EP 799897; WO 01/59503; Chen Y., et al., *Journal of Biomedical Optics* (1997) 2:364–374; and DeRisi J. L. et al. (1997) *Science* 278:680–686.

SUMMARY OF THE INVENTION

Calibration devices for optical scanners and methods for their use are provided. The subject devices are characterized by having a polymeric coating with at least one fluorescent agent, where the devices have minimal local and global nonuniformities. The subject device may also include one or more photobleached regions. In using the subject devices, a surface is illuminated with at least one light source, fluorescence data is obtained from the surface and the optical system is calibrated based upon the obtained fluorescence data. The subject invention finds use in a variety of optical scanners, including biopolymeric array optical scanners. Also provided are kits for use in verifying and calibrating optical scanners.

BRIEF DESCRIPTIONS OF THE DRAWINGS

DETAILED DESCRIPTION OF THE INVENTION

Figure 1:
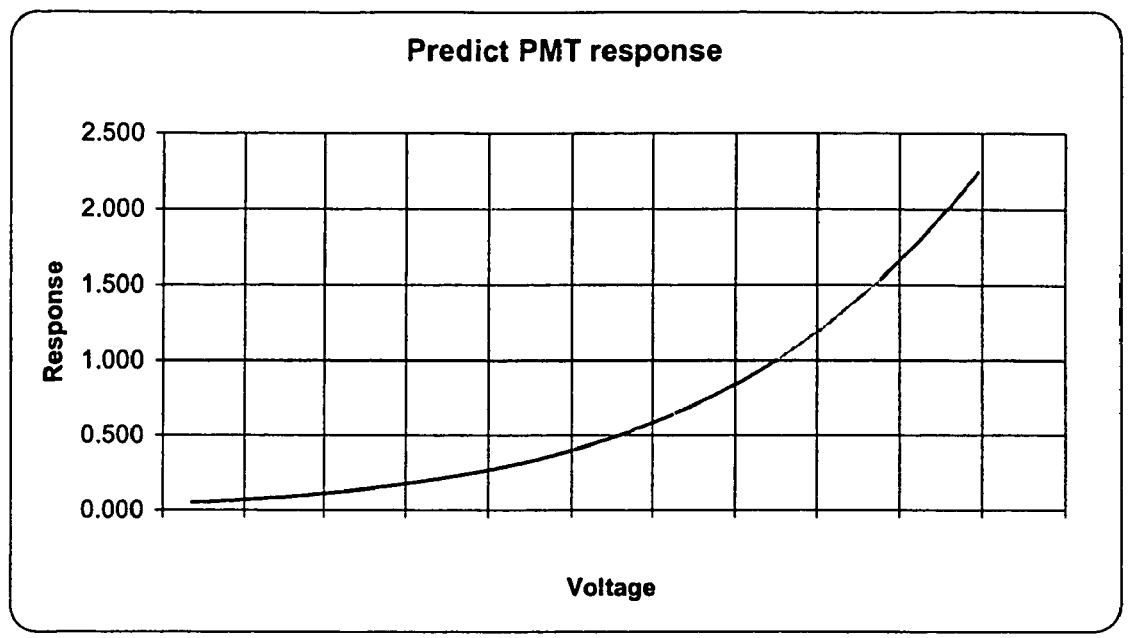
FIG. 1 shows an exemplary optical detector sensitivity/voltage graph.

Calibration devices for optical scanners and methods for their use are provided. The subject devices are characterized by having a polymeric coating with at least one fluorescent agent, where the devices have minimal local and global nonuniformities. The subject device may also include one or more photobleached regions. In using the subject devices, a surface is illuminated with at least one light source, fluorescence data is obtained from the surface and the optical system is calibrated based upon the obtained fluorescence data. The subject invention finds use in a variety of optical scanners, including biopolymeric array optical scanners. Also provided are kits for use in verifying and calibrating optical scanners.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a laser" includes a plurality of such lasers and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Devices

As summarized above, calibration devices are provided for use in calibrating optical scanners, particularly biopolymeric array optical scanners (herein referred to as "optical scanners") and more particularly biopolymeric array optical detectors, lenses, stages and mirrors. In further describing the subject invention, a review of optical scanners suitable for use with the subject invention will be presented first to provide a proper foundation for the invention, followed by a description of the subject calibration devices and methods of using the subject calibration devices to calibrate an optical scanner and scan an array.

Optical Scanners

A variety of optical scanners are known in the art, and particularly optical scanners for scanning arrays are known in the art. By array is meant a collection of separate probes or binding agents each arranged in a spatially defined and a physically addressable manner. In other words, a substrate having a plurality of probes or binding agents stably attached to, i.e., immobilized on, its surface, where the probes or binding agents may be spatially located across the surface of the substrate in any of a number of different patterns. "Probes" or "binding agent" as used herein refers to any agent or biopolymer that is a member of a specific binding pair, where such agents include: polypeptides, e.g. proteins or fragments thereof; nucleic acids, e.g. oligonucleotides, polynucleotides, and the like, as well as other biomolecules, e.g., polysaccharides, etc.

Typically, such array optical scanners include a light source for irradiating light upon the array surface and a light detector for subsequently measuring detectable light from the array surface, e.g., fluorescence emission, etc. Representative biopolymeric array optical scanners include, but are not limited to, those disclosed in U.S. Pat. Nos. 5,585,639 and 6,258,593, the disclosures of which are herein incorporated by reference and commercially available optical scanners such as the Microarray Scanner, model number G2565AA, manufactured by Agilent Technologies, Inc., Palo Alto, Calif., for example.

As described above, the optical scanners suitable for use with the present invention generally include at least one light source for generating at least one coherent light beam at a particular wavelength, a scanning means for scanning the beam over a substrate surface such as an array surface and a light detector for detecting a light produced from the sample regions on the substrate surface, e.g., fluorescence.

The at least one light source is typically a source of light that is capable of irradiating or illuminating the substrate surface, e.g., array surface, with a light that is in the portion of the electromagnetic spectrum to which a photomultiplier tube of the optical scanner is sensitive. Usually, the light is in the ultraviolet, visible or infrared regions, but may include other wavelengths as well if appropriate. Oftentimes, the substrate surface is illuminated by light over a range of wavelengths, where the wavelengths correspond to the fluorescence excitation wavelengths of one or more fluorescent agents, as will be described below, which are bound to the probes or binding agents associated with the surface of the substrate. Where visible light is used, typically a wavelength from about 400 to 700 nm, usually from about 500 to 640 nm and more usually from about 550 to 590 nm is used to illuminate the array surface. Oftentimes, at least two sources of light or two wavelengths are used to illuminate the surface of the substrate. For example, a dual laser scanner may be used, where such a dual laser scanner may include a first laser capable of emitting light in the wavelength from about 570 to 490 nm and a second laser capable of emitting light in the wavelength from about 780 to 620 nm. Any convenient light source may be employed, where suitable light sources include, light emitting diodes, laser diodes, filtered lamps, and the like, where laser light sources are of particular interest and include dye lasers, titanium sapphire lasers, Nd:YAG lasers, argon lasers and any other suitable lasers. More particularly, SHG-YAG lasers and HeNe lasers are typically used as light sources in array optical scanners. The light source(s) oftentimes also includes a scan lens system for focusing the illuminating light to a desired size illumination area on the array, such as described in Smith, W. J., *Modern Lens Design*, McGraw Hill, p. 413.

The light source usually generates a light beam with a width that ranges from about 1 to 200 microns at the focus, usually about 2 to 20 microns and more usually about 5 to 8 microns at the focus.

Usually a scanning means is associated with the light source to scan or raster the light beam in one or more directions over a substrate surface. A suitable scanning means includes, but is not limited to, a mirror, e.g., a scanner mirror as is known in the art, under the control of a motor, such as a galvo-scanner motor also commonly known in the art. The scanning means is usually capable of moving the light beam over a surface having a length from about 4 to 200 mm, usually from about 2 to 150 mm and more usually from about 4 to 125 mm and a width from about 4 to 200 mm, usually from about 4 to 120 mm and more usually from about 4 to 80 mm, for example a 25 mm by 75 mm array or a 22 mm by 22 mm array, as are known in the art. The scan time for a two color, simultaneous scan of a 25 mm by 75 mm array surface usually ranges from about 4 minutes to about 18 minutes, usually from about 6 minutes to about 12 minutes and more usually from about 6 minutes to about 8 minutes.

The optics of the scanner also includes a suitable detector that is capable of detecting light, e.g., fluorescently emitted light, from the substrate, usually in the visible wavelength range, as described above. Any convenient detector may be used, where suitable detectors include, but are not limited to, photodiodes, photomultipliers, photodetectors, phototransistors and the like. An imaging lens system may be associated with the detector, where such a system is designed to image light emitted from the substrate surface, in response to the light source, in an imaging plane alignable with the detector. The imaging system may also include a filter for selectively blocking illumination beam light reflected from the substrate surface.

A microprocessor, operatively connected at least to the scanner motor, controls the movement and position of the mirror and the detector to receive digitized or analog detector signals related to light emission levels measured by the detector.

In a typical scanning operation, the one or more illumination beams are scanned across the array surface, oftentimes simultaneously, exciting fluorescent light emission in each region of each scanned linear array where fluorescently labeled analyte is bound. The emitted light is imaged onto the detector and the intensity of such light emission is measured. The measured intensity associated with each region of the array is recorded and stored with the associated region. After an array has been completely scanned, an output map may be generated, typically automatically by the scanner, which shows the light intensity associated with each region in the array. The output may also include the identity of the molecular species at which fluorescence signal was observed or analyte sequencing information.

Calibration Devices

As noted above, the invention provides devices used for calibrating an optical scanner, such as a biopolymeric array scanner as described above. More particularly, the invention provides devices used to calibrate the optical system's scale factor (i.e., the sensitivity of the system's optical detector), focus position (i.e., the distance between the system's stage and lens(es), dynamic focus (i.e., the rate of speed the stage travels), the scanner mirror and to verify the system's jitter. In general, the subject calibration devices include a substrate and a polymeric layer thereon, usually a single polymeric layer, but in certain embodiments is a plurality of layers, where the polymeric layer includes one or more fluorescent agents. The subject calibration devices may also include at least one region in the polymeric layer that is absent the fluorescent agent and in certain embodiments, the at least one region absent fluorescent agent is photobleached, as will be described in greater detail below.

A variety of substrates, upon which the polymer layer is deposited, may be used with the invention, and the size and shape of the substrate and substrate surfaces, and the substrate material, will necessarily vary according to the particular optical scanner with which it is to be used. Substrates may be flexible or rigid. By flexible is meant that the support is capable of being bent, folded or similarly manipulated without breakage. Examples of solid materials which are flexible solid supports with respect to the present invention include membranes, flexible plastic films, and the like. By rigid is meant that the support does not readily bend, i.e. the support is inflexible. Both flexible and rigid substrates must provide physical support and structure for biopolymeric array fabrication thereon.

The substrates may take a variety of configurations ranging from simple to complex. Thus, the substrate may have an overall slide or plate configuration, such as a rectangular, square or disc configuration. In many embodiments of the subject invention, the substrate will have a rectangular cross-sectional shape, having a length of from about 4 mm to 200 mm, usually from about 4 to 150 mm and more usually from about 4 to 125 mm and a width of from about 4 mm to 200 mm, usually from about 4 mm to 120 mm and more usually from about 4 mm to 80 mm, and a thickness of from about 0.01 mm to 5.0 mm, usually from about 0.1 mm to 2 mm and more usually from about 0.2 to 1 mm. The above dimensions are, of course, exemplary only and may vary as required.

The substrates may be fabricated from a variety of materials. In many situations, a suitable substrate material will be transparent to visible and/or UV and/or infrared light. For flexible substrates, materials of interest include, for example, nylon, nitrocellulose, polypropylene, polyester films, such as polyethylene terephthalate, polymethyl methacrylate or other acrylics, polyvinyl chloride or other vinyl resin, and the like. Various plasticizers and modifiers may be used with polymeric substrate materials to achieve selected flexibility characteristics. For rigid substrates, specific materials of interest include: silicon; glass; rigid plastics, e.g. polytetrafluoroethylene, polypropylene, polystyrene, polycarbonate, and blends thereof, and the like; metals, e.g. gold, platinum, and the like; etc.

As described above, at least one polymeric layer, usually a single polymeric layer such as a thin monolayer (or in certain embodiments a plurality of such layers), having at least one fluorescent agent or moiety (i.e., in those embodiments having more than one layer each layer has at least one fluorescent agent) is layered or coated on a surface of the substrate, typically deposited over substantially the entire area of a surface of the substrate. (The terms "film" and "coating" herein mean a layer of polymeric material positioned in association with a surface. The term "layer" thus encompasses both "coating" and "film".) A variety of polymers may be used, where such a polymer will typically be rigid, thermally stable, photo non-reactive, non-fluorescent, chemically resistant and substantially transparent across the wavelength region of interest. Representative materials suitable for use include, but are not limited to, acrylates such as polyacrylates, polymethyl-methacrylate, polyacrylamide, polyacrylic acid, epoxides such as polyglycidoxyether polyethylene oxide, polyprolyleneoxide, urethanes such as various polyurethanes, and may also include polycarbonates, polyolefins, polyetherketones, polyesters, polystyrenes, polyethylstyrene, polysiloxanes, and the like, and copolymers thereof.

The polymer coating has a substantially uniform thickness, i.e., the thickness of the polymer layer does not vary significantly across its area, but rather is substantially constant. By significantly is meant that the deviation in the thickness across the area of the polymer layer is usually less than about 0.05% to about 20% and more usually less than about 0.1% to about 10%. More particularly, the thickness of the polymer layer usually ranges from about 0.25 microns to about 10 microns, usually from about 0.40 microns to about 7 microns and more usually from about 0.40 microns to about 1 micron with a deviation of less than about 0.05% to about 20% and more usually with a deviation of less than about 0.1% to about 10%. It will be apparent that using a confocal optical system enables use of such minimal polymer layer thicknesses.

The polymer coating may be formed by any convenient method, including, but not limited to, draw coating, roller coating, electrocoating, dip coating, spin coating, spray coating, or any other suitable coating technique wherein a solution or suspension of the polymer is deposited on the substrate surface, where spin coating is of particular interest. Oftentimes, deposition of the polymer layer will be followed by drying via vacuum, forced air oven, convection oven, or other drying technique.

As mentioned above, a feature of the polymer layer (i.e., each polymer layer if more than one layer used) is the presence of at least one fluorescent agent or moiety, where in many embodiments at least two fluorescent agents or more are used, for example three, four or more fluorescent agents may be employed. By fluorescent agent is meant any dye, pigment or the like capable of emitting radiation or fluorescence in response to radiation excitation thereof. Typically, the radiation or light absorbed and emitted from the fluorescent agent, i.e., the response radiation, (the wavelength of the response radiation) is chosen to be in the portion of the electromagnetic spectrum to which a photomultiplier tube of the optical scanner is sensitive. Usually, the light absorbed and emitted from the fluorescent agent is in the ultraviolet, visible or infrared regions, but may include other wavelengths as well if appropriate.

The particular fluorescent agent(s) used may vary depending on a variety of factors, where such factors include the particular optical scanner used, the probe or binding agent bound to the scanned substrate surface such as a biopolymer array, the excitation and/or response wavelength, and the like. The fluorophoric moieties or fluorophores of the fluorescent agents, may be cyclic, or polycyclic, particularly polycyclic, aromatic compounds having at least two rings, usually at least three rings and not more than six rings, more usually not more than five rings, where at least two of the rings are fused and in certain embodiments at least three of the rings are fused, where usually not more than four of the rings are fused. The aromatic compounds may be carbocyclic or heterocyclic, particularly having from one to three, more usually one to two nitrogen atoms as heteroannular atoms. Other heteroannular atoms may include oxygen and sulfur (chalcogen).

The rings may be substituted by a wide variety of substituents, which substituents may include alkyl groups of from one to six carbon atoms, usually from one to two carbon atoms, oxy, which includes hydroxy, alkoxy and carboxy ester, generally of from one to four carbon atoms, amino, including mono- and disubstituted amino, particularly mono- and dialkyl amino, of from 0 to 8, usually 0 to 6 carbon atoms, thio, particularly alkylthio from 1 to 4, usually 1 to 2 carbon atoms, sulfonate, including alkylsulfonate and sulfonic acid, cyano, non-oxo-carbonyl, such as carboxy and derivatives thereof, particularly carboxamide or carboxyalkyl, of from 1 to 8 or 1 to 6 carbon atoms, usually 2 to 6 carbon atoms and more usually 2 to 4 carbon atoms, oxo-carbonyl or acyl, generally from 1 to 4 carbon atoms, halo, particularly of atomic number 9 to 35, etc.

Specific fluorescent agents of interest include at least one of, but are not limited to: xanthene dyes, e.g. fluorescein and rhodamine dyes, such as fluorescein isothiocyanate (FITC), 2-[ethylamino)-3-(ethylimino)-2-7-dimethyl-3H-xanthen-9-yl] benzoic acid ethyl ester monohydrochloride (R6G)(emits a response radiation in the wavelength that ranges from about 500 to 560 nm), 1,1´,3,3,3´,3´-Hexamethylindodicarbocyanine iodide (HIDC) (emits a response radiation in the wavelength that ranged from about 600 to 660 nm), 6-carboxyfluorescein (commonly known by the abbreviations FAM and F),6-carboxy-2=,4=,7=,4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, etc.

Where at least two or more are agents are used, any combination of suitable agents may be used, where particular combinations of interest include R6G, i.e., 2-[ethylamino)-3-(ethylimino)-2-7-dimethyl-3H-xanthen-9-yl] benzoic acid ethyl ester monohydrochloride and HIDC, i.e., 1,1,3,3,3',3'-Hexamethylindodicarbocyanine iodide; Cy3 (Indocarbocyanine) and Cy5 (Indodicarbocyanine); and other suitable combinations, where combinations of green and red dyes are of particular interest.

A feature of the at least one fluorescent agent is that it is distributed substantially uniformly throughout the polymer. In other words, the at least one fluorescent agent is homogenously dispersed throughout the polymer such that the concentration of the fluorescent agent(s) is substantially constant throughout the polymer layer. For example, the at least one fluorescent agent is distributed throughout the polymer such that the ratio of % fluorescent agent to % polymer for any given area is substantially the same for all areas of the polymer layer. It will be apparent that if more than one fluorescent layer is used, all fluorescent agents employed will be distributed substantially uniformly throughout the polymer. Specifically, any variation in fluorescent agent distribution that is present typically does not exceed from about 1 ppm to 5000 ppm, usually does not exceed from about 100 ppm to 800 ppm and more usually does not exceed from about 150 ppm to 180 ppm, where such variation is determined by determining dye concentration prior to coating using fluorescent or absorption measurements employing typical laboratory instruments (e.g., Fluorimeter or UV\V spectrometer).

The concentration of the fluorescent agent (i.e., the concentration of each fluorescent agent if there is more than one) may vary depending on the particular scanning detector to be calibrated, the type and/or number of fluorescent agents used, etc. However, typically, the final concentration of fluorescent agent will range from about 1 ppm to 5000 ppm, usually from about 100 to 500 ppm and more usually from about 150 to 200 ppm. It will be apparent that the fluorescent agent's concentration is variable, depending on the final thickness of the polymeric coating, where such concentration is determined to provide approximately the same number of fluorescent molecule per unit area regardless of the coating thickness, e.g., a 50 micron film will have a 100 fold more fluorescent molecules than a film having a thickness of 0.5 microns. However, each fluorescent molecule's concentration will be dependent on its efficiency, i.e., a dye with high quantum efficiency may have a lower concentration than a fluorescent molecule with a lower efficiency. In other words, the subject calibration devices have a consistent intensity in all wavelength ranges, rather than a consistent number of fluorophores.

Another feature of the subject calibration devices is that the local and global fluorescence variations are minimal, i.e., the local and global nonuniformities are minimal. By local variations or nonuniformities is meant that the light emitted from each pixel in a certain area or region, (pixel size ranges from about 2 to 15 microns) i.e., the number of photons detected in each pixel of the calibration device is substantially the same or constant, where it will be obvious that the exact local and global variation or nonuniformity requirement of the intensities of light emitted may vary depending on a variety of factors such as the specific device to be calibrated and the like. In general, the local and global nonuniformities are minimized to a degree sufficient to enable calibration, as described below, of the particular optical scanner employing the subject device.

In regards to local nonuniformities, in certain embodiments of the subject device the difference or deviation between the response radiation or light emitted from each pixel in a certain area of the subject device is typically less than about 5%, usually less than about 2.5% and more usually less than about 1%. Usually, the local nonuniformity is based upon a local area having about 5 to 10 pixels, usually about 7 to 9 pixels, where each pixel ranges in size from about 2 to 15 microns, usually from about 4 to 12 microns and usually from about 5 to 10 microns. As such, the response radiation or number of photons emitted from a first pixel is substantially the same as the number of photons emitted from each of five to ten substantially adjacent pixels. In other words, the quantity of light emitted from between about five to ten substantially adjacent pixels will have minimal variation or nonuniformty, i.e., the variation is typically be less than about 5%, usually less than about 2.5% and more usually less about 1%.

The global variation or nonuniformity is similarly minimal. By global variation or nonuniformity is meant a statistically relevant value (mean, median, etc.) corresponding to all or substantially all of the individual local variations of the entire calibration device. As noted above, the exact global nonuniformity requirement may vary depending on a variety of factors. In certain embodiments, the global nonuniformity is typically less than about 5%, usually less than about 3.5% and more usually less than about 2.5%. In other words, the quantity of light emitted from each local area will be substantially the same as or similar to the quantity of light emitted from each other local area, i.e., the variation or nonuniformity is typically less than about 5%, usually less than about 3.5% and more usually less than about 2.5%.

As described above, the calibration devices of the subject invention may also include at least at least one region in the polymeric layer that is absent fluorescent agent. By absent is meant that there is less than about 5% of the molar amount of fluorescent agent in active form (i.e., the molar amount of fluorescent agent that fluoresces), usually less than about 2% the molar amount of fluorescent agent in active form. The at least one region absent fluorescent agent may thus include photobleached regions and/or background regions, as will be described below.

As mentioned, the subject devices may include one or more photobleached region or feature. In other words, a photobleached region is typically a region made of a material that includes a bleached fluorescent agent(s), where such bleaching reduces or attenuates the fluorescence of the fluorescent agent(s) by at least about 40% to 60%. For example, the at least one photobleached region or feature will usually be made of the same polymer material and fluorescent agent(s) used to produce the polymeric calibration layer, i.e., the fluorescently dispersed polymer layer described above. Generally, the calibration device will include a plurality of such photobleached regions or features positioned in predetermined locations on the surface of the device. For example, on a calibration device having a width of about 25 mm and a length of about 75 mm, about 1 to 5000 photobleached regions may be positioned in various locations, more typically about 200 to 750 photobleached regions may be positioned in various locations. Usually, a photobleached region has a size substantially equal to the size of about 1 to 3 pixels in at least one dimension on the device. More specifically, where the photobleached regions or features are rectangular, typically the length ranges from about 175 to 225 microns, usually from about 190 to 210 microns and the width typically ranges from about 5 to 15 microns, usually about 7 to 9 microns and, for an example having about 1000 features on a 25 mm by 75 mm calibration device, about 250 to 270 of these features are positioned horizontally and about 670 to 690 of these features are positioned vertically.

The subject devices may also include one or more background areas or features, as mentioned above. The one or more background area is an area or region that is outside of the calibration area, i.e., an area that does not include fluorescent agents (whether photobleached or not), i.e., that is absent fluorescent agent. Usually, a background region will be a region of the calibration device off of the surface of the device, i.e., not on the surface of the device, e.g., one or more edges of the substrate of the calibration device, negative space such as air space, and the like.

Methods of Use

As summarized above, the subject invention also provides methods for calibrating an optical scanner. More specifically, methods are provided for calibrating an optical system associated with an optical scanner and in particular a biopolymeric array optical scanner. In general, a surface is illuminated with at least one light source, e.g., the surface of the calibration device described above. In other words, the polymeric layer having at least one fluorescent agent or moiety dispersed therethrough and having minimal local and global nonuniformities is illuminated with at least one light source and fluorescent data from the surface is obtained. Oftentimes, the calibration device is positioned on the support stage or the like such that the substrate side of the device (as distinguished from the polymeric coated side) is faced up. In other words, light is directed first through the substrate side of a subject calibration device. An optical system is then confirmed (in other words no adjustments are made) or the system is adjusted or calibrated based upon this obtained fluorescence data. By adjusted or calibrated is meant that one or more of the following is confirmed and/or adjusted: (1) scale factor (i.e., the sensitivity of the optical detector is adjusted), (2) the focus position (i.e., the distance between the stage and one or more lenses of the system is adjusted), (3) the dynamic focus (i.e., the rate of speed the stage travels is adjusted), (4) the scanner mirror (i.e., the synchronicity of the light beams is adjusted), and (5) the jitter, where each of these will be discussed in greater detail below.

Thus, the first step in all of the subject methods for calibrating or adjusting certain optical components of an optical scanning system is to illuminate a surface with at least one light source, and more particularly irradiate a surface with a source of excitation radiation, where the surface includes at least one fluorescent agent dispersed therethrough and which has minimal local and global nonuniformities. In other words, a surface, such as the fluorescently-infused polymer layer of the calibration device having minimal local and global nonuniformities, as described above, is irradiated with one or more light beams having specific wavelengths, where the one or more light beams are used to excite the one or more fluorescent agents associated with the surface being illuminated. It will be understood that unless otherwise noted, the surface scanned according to the methods described below is a non-photobleached area. That is, for the detector, lens, stage and mirror calibration methods, the area scanned does not include photobleached regions, i.e., either the calibration device does not include photobleached regions or such photobleached areas are not scanned or the data therefrom is not used in the subject methods to calibrate the optical detector, lens, stage and mirror. However, as will be described below, for the subject methods relating to jitter verification, the area(s) scanned are photobleached areas. As mentioned above, in many embodiments, the light is directed through the substrate side of the calibration device first, i.e., light is directed through the substrate and then to the polymeric layer.

More specifically, a calibration device is provided having a polymer coating having at least one fluorescent agent therein and minimal local and global fluorescence variations, i.e., the local and global nonuniformities are minimal, such as a calibration device described above. As noted above, by local variations or nonuniformities is meant that the light emitted from each pixel in a certain area or region, (pixel size ranges from about 2 to 15 microns) i.e., the number of photons detected in each pixel of the calibration device is substantially the same or constant. More specifically, the difference or deviation between the response radiation or light emitted of pixels of the subject device is typically less than about 5%, usually less than about 2.5% and more usually less than about 1%. Usually, the local variation is based upon a local area having about 5 to 10 pixels, usually about 7 to 9 pixels, where each pixel ranges in size from about 2 to 15 microns, usually from about 4 to 12 microns and usually from about 5 to 10 microns. As such, the response radiation or number of photons emitted from a first pixel is substantially the same as the number of photons emitted from each of five to ten substantially adjacent pixels. In other words, the quantity of light emitted from between about five to ten substantially adjacent pixels will have minimal variation, i.e., the variation is typically be less than about 5%, usually less than about 2.5% and more usually less about 1%. The global variation or nonuniformity is similarly minimal. As described above, by global variation or nonuniformity is meant a statistically relevant value (mean, median, etc.) corresponding to all or substantially all of the individual local variations of the entire calibration device. Typically, the global variation is less than about 5%, usually less than about 3.5% and more usually less than about 2.5%. In other words, the quantity of light emitted from each local area will be substantially the same as or similar to the quantity of light emitted from each other local area, i.e., the variation is typically less than about 5%, usually less than about 3.5% and more usually less than about 2.5%.

Each light source will typically produces a coherent light beam, e.g., the light source will typically be a laser light source, and the like. More typically, the light sources will include two laser light sources or produce two different beams of light (i.e., beams of light of two different wavelengths, e.g., a red laser light source and a green laser light source.

Typically, each light beam having an excitation wavelength that is within the ultraviolet, visible or infrared spectrum illuminates the surface of the calibration device described above. In general, the at least one light beam illuminates the surface with light of a selected wavelength, where the selected wavelength is usually at or near the absorption maximum of the particular fluorescent agent being illuminated or excited. Illuminating or exciting a fluorescent agent at such a wavelength produces the maximum number of photons emitted at the emission wavelength. In certain embodiments of the subject methods, light beams from at least two light sources are used, where the light beams from the various light sources are of different wavelengths, each source usually corresponding to fluorescent excitations of the different fluorescent agents being illuminated and excited. In other words, the wavelengths of the light beams are at or near the absorption maximum of the fluorescent agents illuminated. For example, light from a first light source illuminates the surface with light in a wavelength ranging from about 500 to 560 nm corresponding to the fluorescence excitation of about 500 to 560 nm of a first fluorescent agent, e.g., of 2-[ethylamino)-3-(ethylimino)-2-7-dimethyl-3H-xanthen-9-yl] benzoic acid ethyl ester monohydrochloride, and light from a second light source illuminates the surface with light in a wavelength ranging from about 600 to 660 nm corresponding to the fluorescence excitation of about 600 to 660 nm of a second fluorescent agent, e.g., 1,1,3,3,3',3'-Hexamethylindodicarbocyanine iodide. Where more than one light source is used, the light sources may illuminate the surface at the same or different time, but usually the light sources will illuminate the surface simultaneously.

A feature of the subject methods is that substantially the entire surface (excluding the photobleached regions, if present, as mentioned above) is illuminated by the at least one light source. By substantially entire surface is meant that almost the total surface area is illuminated, where such an illumination area may be as great as about 70% of the entire surface area, usually as great as about 75% of the entire area and more usually as great as about 80% of the entire area is illuminated. In other words, usually one or more light beams are swept or rastered across a substrate surface, as opposed to simply illuminating one discrete region. For example, in those embodiments using a calibration device as described above, e.g., a 25 mm by 75 mm calibration device, one or more light beams will usually scan or raster over an area having a width ranging from about 10 to 30 mm, usually about 15 to 25 mm and a length ranging from about 50 to 70 mm, usually from about 55 to 65 mm. In those embodiments where the calibration device has dimensions of about 22 mm by 22 mm, one or more light beams will usually scan or sweep over an area having a width ranging from about 10 to 20 mm, usually about 15 to 20 mm and a length ranging from about 10 to 20 mm, usually from about 15 to 20 mm, where such illumination usually occurs in a predefined pattern, oftentimes in a linear pattern. The surface may be illuminated by more than one light source at the same or different times. In other words, a surface or a region of the surface may first be illuminated by a first light source and then subsequently illuminated by a second light source. Usually, a two color, simultaneous illumination or scan of a 25 mm by 75 mm surface usually is performed in about 5 to 10 minutes and more usually in about 7 to 9 minutes.

Once substantially the entire surface has been excited by one or more light sources, the next step is to detect fluorescence from the surface. More specifically, data are acquired from the surface, where such data corresponds to the light emitted, i.e., the intensity of light emitted, from the at least one fluorescent agent associated with the surface. Thus, one or more fluorescent agents are excited by the illumination from the one or more light beams, where each fluorescent agent emits light of a certain wavelength, at a certain intensity. The intensity of light emitted from each pixel is detected and measured by an optical detector such as a photomultiplier tube (PMT) or the like, where the PMT generates a current proportional to the number of photons that reach it. The PMT typically generates a current ranging from about 500 nanoamps to 50 microamps within its range of operation, more usually from about 1 microamp to 10 microamps. Output from the detector is used to calibrate the detector, or make certain other optical system adjustments, as will be described below, where the adjustments may be made manually or automatically, for example by an operatively associated microprocessor.

As mentioned above, each of the methods described below can be utilized separately or in any combination during the scanner optimization process, however they may be interrelated, as will be apparent to one of skill in the art.

1. Scale Factor Calibration

As described above, data from the above described scanning method may be used to calibrate the scale factor of the optical system, i.e., used to verify the sensitivity of the optical detector of the system and, if necessary, calibrate or adjust the sensitivity of the detector.

As such, following the above described scan of the calibration device, an empirical calibration value is calculated based upon the intensity of the signal, where such a calibration value is defined as the number of photons in a pixel to fluorophores per square micron. Thus, current corresponding to the intensity of light emitted per pixel is converted to digital counts and such counts are used to determine a calibration value for the respective optical detector. This empirically derived calibration value and corresponding digital signal are then compared to a reference calibration value/signal function. In other words, the empirically derived calibration value/signal is compared to a predetermined or reference value that is a function dependent upon the particular fluorescent agent used, the type of optical detector employed, the area of the pixel, and the like. The optical system's gain is then adjusted in response to this comparison. In other words, the gain is adjusted to more closely approximate the reference calibration value. The values obtained from a single calibration device may be used to calibrate a plurality of optical systems or scanners in parallel.

More specifically, a detector such as a photomultiplier tube is used to detect the intensity of the light emitted from the one or more fluorescent agents, where such intensity is in the form of a voltage measurement. Such intensity is relayed to a microprocessor, i.e., a microprocessor operatively associated with the optical scanner containing the detector, where such a microprocessor is under the control of a software program and carries out all of the steps necessary to determine if the detector is within specification or if it needs adjustment. The microprocessor may also performs the steps necessary to adjust the detector.

The detector is calibrated or adjusted by altering the voltage of the detector, where the voltage determines the sensitivity of the detector. In other words, an empirical calibration value is determined according to the method described above, i.e., the signal from the PMT operated at a known voltage is obtained, and this empirical value is compared to a reference or standard value. If the voltage relating to the empirical calibration value is different, i.e., substantially or significantly differs, from the reference or predetermined voltage, the sensitivity or voltage of the detector is altered to change the response of the detector.

For example, a typical photomultiplier response is shown in FIG. 1. FIG. 1 shows an x-y graph having photomultiplier sensitivity values or response (defined as photons per fluorophores, where the photons counted are typically normalized to fluorescent molecules as opposed to area) on the y-axis and voltage on the x-axis. A typical plot is represented by a line having an increasingly positive or ascending slope. Thus, a mathematical function described by this calibration curve value and corresponding voltage can be derived and which allows extrapolation of the proper response for the calibrated detector. The photomultiplier voltage, i.e., sensitivity, is adjusted if the signal from the photomultiplier is different from the optimum signal. The calibration is complete for the detector when the relationship between the extrapolated value and the real values are within a certain range, for example less than a certain predetermined percentage, such as 1%, etc.

2. Focus Position Calibration

Figure 3:
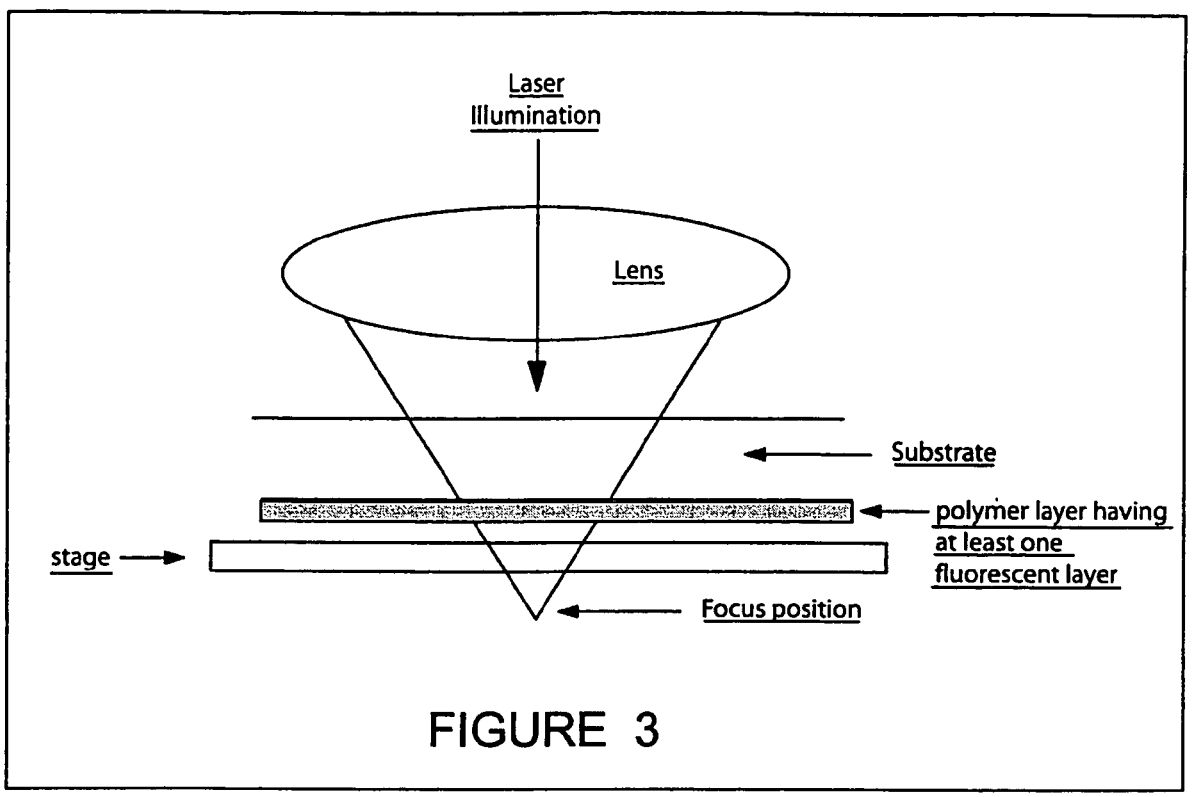
FIG. 3 shows an exemplary embodiment of a laser beam being illuminated or directed through a lens to a focus position according to the subject invention.

In addition to, or independent of, the above described methods for calibrating the scale factor of the system, methods for calibrating or adjusting the one or more scanning stages (i.e., the distance between the scanning stage and an optical lens)of an optical scanner are also provided so as to adjust the focus position of the laser(s) relative to the surface of a scanned object, i.e., adjust the stage position to optimize the intensity of the light detected, where such intensity may not correspond to the maximum of the fluorescence signal collected. FIG. 3 illustrates the subject method, whereby a laser beam is illuminated or directed through a lens to a focus position.

Thus, in certain embodiments of the subject methods, the focus position of the optical system is evaluated and adjusted, if necessary. In other words, the depth of the focus of the illuminated light is verified and/or adjusted to an optimal focus position such that at such an optimal position or distance, the intensity of light from one or more channels, as measured by the detector, will be optimized and have the qualities necessary for an optimum scan, e.g., minimal noise in an optimum two color scan. It will be apparent that the device, i.e., the calibration device, used to check and/or adjust the focal position must have minimal local and global nonuniformities so that the intensities detected and measured are a function of the focal position, and not the variation in the scanned device, i.e., the area scanned must be able to provide a consistent signal.

Thus, after the provision of a calibration device having a polymer coating with at least one fluorescent agent associated therewith and local nonuniformities of less than about 5%, usually less than about 2.5% and more usually less about 1% and global nonuniformities of less than about 5%, usually less than about 3.5% and more usually less than about 2.5%, the calibration device is scanned with at least one light source, as described above, at various depths. That is, the light beam will scan the surface of the calibration device, where a number of different focal positions are used to scan the surface. As will be apparent, the scanned area must be of sufficient proportion to enable acquisition of consistent signal. More specifically, scanning a small, localized area over a significant period of time, i.e., an amount of time necessary to scan at various focus depths, may result in the fluorescence fading in a particular scanned area, thus yielding unreliable signals. As such, an area of the calibration device of about 5 mm to about 20 mm, usually about 10 mm to about 100 mm and more usually about 20 mm to about 60 mm is scanned by at least one light source, usually two light sources such as a red laser and a green laser, as described above, where such a scan typically takes from about 4 minutes to about 18 minutes, usually from about 6 minutes to about 12 minutes and more usually from about 6 minutes to about 8 minutes.

After the area has been scanned at various depths, i.e., various focal positions, the focal position providing the optimum signal is selected, and the distance between the optical or focusing lens and the scanning stage is calibrated or adjusted to provide the optimum focal depth, where such a focal distance is then stored in the optical system's memory, i.e., stored in a microprocessor operatively associated with the optical system, such that the optical system will scan subsequent devices at this focal distance. In other words, an optimal focus depth is determined based upon the above described scan and the position of the fluorescent coated surface relative to the scanning lenses of the optical system, i.e., the distance between the stage and lens(es), is then adjusted by adjusting the position of the scanning stage to correspond to this optimal configuration to provide the optimum scanning depth for subsequent scans, e.g., subsequent biopolymeric array scans.

3. Dynamic Focus Calibration

Methods are also provided for verifying and/or calibrating or tuning the dynamic focus of the scanning light beams, i.e., adjusting the rate at which the optical stage travels, of an optical scanning device, where such a stage is configured to provide a platform or area onto which a scanned object such a biopolymeric array may be placed during a scanning procedure. The stage aligns the scanned object in a certain position to correspond with the scanning light beam(s). That is, in use, the stage is moved to align an optical system or scanning plane to correspond to an area of the scanned object to be scanned such as a certain linear array area on a substrate. Thus, it will be apparent that the focus of the system is dependant upon certain stage parameters associated with the optical stage such as the rate of movement of the stage, etc. For example, if the stage is moved too quickly or is out of alignment, the scan will be out of focus.

As mentioned above, the first step in the subject methods for verifying and/or adjusting the rate of speed of a stage of an optical system is to provide a device having minimal local and global nonuniformities, as described above.

After the provision of the above described calibration device, a series of horizontal scan lines or planes are scanned by at least one light source, typically two, as noted above. Next, the oscillation of the detected intensity image of these scanned horizontal planes is measured. More specifically, the oscillation over about 75 to 100 pixels, usually over about 90 to 110 pixels and more usually over about 95 to 105 pixels is measured. If the oscillation is less than about 0.15%, usually if it is less than about 0.1%, no adjustments to the rate of speed of the stage is made. If the oscillation is greater than about 0.15%, usually if it is greater than about 0.1%, the rate of speed of the stage is adjusted, i.e., the rate is increased or decreased so as to optimize the focus of the system, where such a rate of speed is then stored in the optical system's memory, i.e., stored in a microprocessor operatively associated with the optical system, such that the optimum rate of movement of the stage will be fixed at this adjusted rate for subsequent scans.

4. Scanner Mirror Calibration

Figure 2:
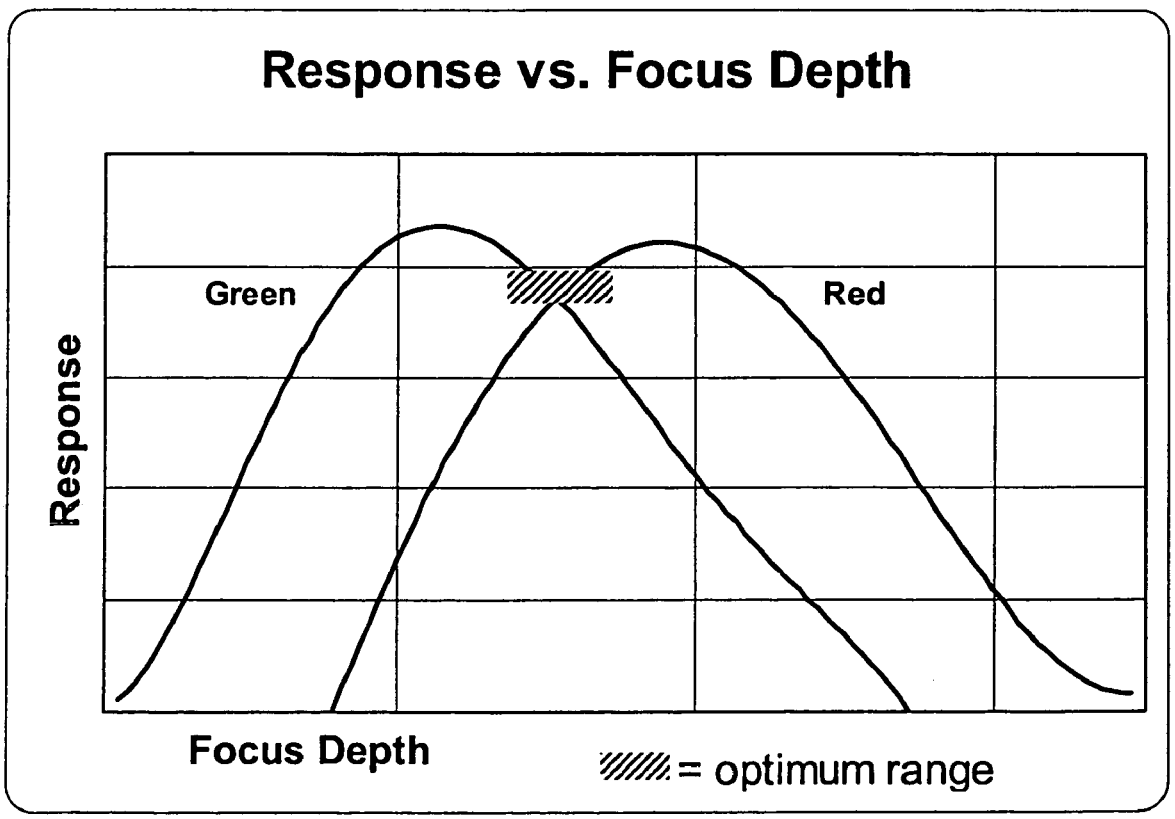
FIG. 2 shows exemplary response curves according to the subject invention.

Methods are also provided for verifying and calibrating one or more optical or scanner mirrors associated with the optical system, as described above, where such scanning mirrors are used to direct one or more light sources to a focus lens of the optical system, as described above, typically by pivoting the mirrors to position the light beam(s) to optimize the associated response. As mentioned above, in a two color scan, i.e., a scan using more than one light source or beam, e.g., a red laser and a green laser, typically the two lasers scan or raster a scan area simultaneously, or alternatively the surface is moved in a controlled manner with a motorized stage. Thus, the scanner mirrors, which dictate the alignment and positioning of the laser beams, must be synchronized to enable such a simultaneous scan, i.e., the scanning mirrors must direct the two lasers to substantially the same location at the substantially same time. FIG. 2 show exemplary response curves related to the alignment of laser light, by adjusting the alignment of the two beams, the focus depth for the two channels is optimized at a value that gives the lowest noise such as depicted in FIG. 2 as the region of overlap of the two channels. Synchronicity or calibration of the scanner mirrors according to the subject invention is thus accomplished by scanning a device having minimal local and global nonuniformities and evaluating the relationship between the intensity profiles or scan images of the different lasers and comparing the relationship of the scans to a predetermined relationship. In other words, where a green laser and a red laser are used for a simultaneous scan, an optimum scan, as it relates to the scanner mirrors, can be characterized by evaluating the relationship between the location of the green channel fluorescent peak and the red channel fluorescent peak. For example, the response at specific focus positions for a first laser and a second laser, such as a red and green laser, is evaluated and compared to a predetermined relationship. As FIG. 2 shows, the overlap between a first channel and a second channel, such as a red channel and a green channel, is optimized at a certain point or focus depth, so as to produce a scan with minimal noise. Thus, the beams or peak positions are adjusted by rotating or translating the mirror(s) in the laser beam path, where this alignment is a function of the focus position/response generated by the above described method, which is compared to a predetermined relationship and adjusted based upon any deviation from such a predetermined relationship. More specifically, if the lasers are not synchronized, i.e., out of alignment, the relationship of the channels differs from a predetermined relationship and are adjusted to approximate the predetermined relationship.

Accordingly, a device having minimal local and global nonuniformities, i.e. a calibration device as described above, is provided and scanned with at least two light sources, typically having different wavelengths, e.g., two laser light sources such as a red laser and a green laser, where such methods for scanning such a device with two light sources is described above and will not be repeated here.

After the calibration device is scanned by the two light sources, e.g., a red laser light source and a green laser light source, the intensity profiles for each color scan is evaluated. That is, the relationship between the two color scans is determined and compared to a predetermined relationship, where such a predetermined relationship is based upon a variety of factors such as the wavelengths of the two laser light sources (red and green as used herein), the time of the scan, the size of the area scanned, and the like.

Specifically, the location of a first channel peak or maximum intensity, such as a green channel peak, is determined and the location of a second channel peak or maximum intensity, such as a red channel peak, is determined, where the relationship between the locations of the two peaks is evaluated and compared to a predetermined channel peak relationship. The change or deviation from the predetermined relationship is a manifestation of the lateral movement of the laser beam across the rigidly fixed focusing lens. If the relationship is substantially similar to the predetermined relationship, no adjustments to the scanning mirrors are made. If, however, the relationship substantially differs from the predetermined relationship, adjustments to one or more mirrors are made, i.e., the direction or pivotal motion of one or more mirrors is adjusted. If adjusted, the adjusted configuration of the one or more mirrors is fixed, at the adjusted configuration for subsequent scans.

5. Jitter Verification

Also provided are methods for verifying the jitter of an optical scanner. More specifically, methods are provided for verifying the jitter of an optical system associated with an optical scanner and in particular a biopolymeric array optical scanner. By jitter is meant the time interval between each successive pulse in a pulse train. In other words, a pulse train of the above described light sources, i.e., laser light sources, should have minimal jitter between the pulses so that in a scan using more than one light source, i.e., more than one light beam for example a red laser and a green laser, the beams reach the scan surface simultaneously (i.e., the red and green channels are synchronized). In such a method, the jitter is typically verified or confirmed to be in a particular acceptable range, where such a range will not substantially interfere with the performance or imaging of the optical scanner. In other words, the jitter is usually not adjusted, but rather confirmed or verified to be suitable. The calibrations, alignments and focusing methods outlined above determine the associated jitter in the scanning instrument. In other words, jitter is a function at least of the alignment or calibration of the optical system's other optical components (described above) and thus if jitter is found to be out of specification, one or more of the above described methods for calibrating the optical system is employed to make the appropriate adjustment(s) to the system. Following such adjustments, the jitter is again verified or confirmed.

In this particular method for verifying the jitter of an optical system or rather the deviation in jitter between two channels, a device having a pattern of photobleached regions is provided, such as the calibration device described above having one or more photobleached regions. In other words, a calibration device having a polymer coating with one or more fluorescent agents bleached in a pattern, for example bleached from a first calibration device edge to a second calibration device edge, or the like, to produce one or more photobleached regions or features is employed to verify the jitter of an optical system.

The calibration device is scanned by two light sources, e.g., a red laser and a green laser. More particularly, a pattern of photobleached areas is scanned simultaneously by a red laser and a green laser. As mentioned above, the mechanical stage directs or moves the calibration device into the appropriate focusing position to align the area to be scanned with the scanner light beams. Thus, once positioned, the photobleached area(s) are scanned and an intensity profile for each channel is produced. In other words, an intensity profile including the channel peaks or maximum wavelength intensity is produced for both the red and green channels. The relationship between the red channel peak and the green channel peak is analyzed, where such a relationship generated by the simultaneous scanning of photobleached areas is a function of the jitter of the optical system, i.e., is dependent on the amount of jitter in each pulse train. The relationship is compared to a predetermined value or standard to determine the amount of deviation of jitter in the optical system relative to the standard. In other words, the amount of jitter of the optical system is determined by scanning the photobleached patterns of the subject devices. The optical system is determined to be suitable for use, i.e., the scanning lasers are capable of scanning a device such as a biopolymeric array substantially simultaneously, if the jitter is less than a certain predetermined jitter value or standard. That is, the time between pulses in each pulse train are substantially synchronized such that a simultaneous scan using the above tested lasers, i.e., red and green lasers, is verified. As mentioned, if the jitter substantially deviates from the predetermined value, the system is calibrated using one or more of the above described methods for calibrating certain optical components of the scanner's optical system, e.g., dynamic focus calibration, and the jitter is then again verified.

Background Signal Subtraction

The subject invention also includes background subtraction methods for subtracting a value from the emitted fluorescence values, where such subtracted value corresponds to background signal. By background signal is meant the amount of signal generated from one or more non-fluorescent areas. Background signal may be a function of the "noise" of the optical scanner, the polymeric material, the substrate material, particular solutions, electronic noise, reflections or scattering from surface or particles, and the like.

Thus, the background signal is determined, where the background signal is defined as signal generated from outside of the calibration area, i.e., does not include fluorescent agents (whether photobleached or not). Usually, a background region will be a region of the calibration device off of the surface, i.e., not on the surface, of a calibration device being scanned, e.g., one or more edges of the substrate of the calibration device, negative space such as air space, and the like.

Accordingly, the signal from a background area is detected by an optical detector and is calculated, usually as a statistically relevant value. In certain embodiments, the background signal will be predetermined and stored in the memory of an optical system. Regardless of whether the background signal is determined or predetermined, the background signal is then subtracted from the value corresponding to the intensity of light emitted from the fluorescent calibration regions (photobleached and/or non-photobleached areas) on the calibration device. The final value represents a background corrected signal corresponding to the intensity of light per pixel due to the fluorescent agent.

Methods of Use for Scanning an Array

Also provided by the subject invention are methods for calibrating an optical scanner and subsequently using the calibrated scanner to scan an array, more specifically a biopolymeric array, e.g., a nucleic acid array. More specifically, in the subject methods, an optical scanner is calibrated, i.e., a detector, a lens, a stage and/or a mirror of an optical scanner is adjusted, an array is provided and a hybridization assay is performed with the array and one or more samples or agents of interest. The hybridized array is then optically scanned by the calibrated scanner, where such steps may be performed serially or simultaneously.

Accordingly, an optical scanner, e.g., a biopolymeric array optical scanner, is calibrated. More specifically, one or more of the following is confirmed and/or adjusted: (1) scale factor (i.e., the sensitivity of the optical detector is adjusted), (2) the focus position (i.e., the distance between the stage and one or more lenses are adjusted), (3) the dynamic focus (i.e., the rate of speed the stage travels is adjusted), (4) the scanner mirror (i.e., the synchronicity of the light beams is adjusted), and (5) the jitter, as described above. In other words, generally, a calibration device is illuminated with at least one light source, e.g., the calibration described above, in other words the polymeric layer having at least one fluorescent agent or moiety dispersed therethrough and having minimal local and global nonuniformities, is illuminated with at least one light source, and fluorescent data from the calibration device is obtained, where such data may include subtracting background values therefrom, as mentioned above.

In one embodiment, the scale factor of the optical system is calibrated, i.e., an optical detector is confirmed (in other words no adjustments are made) or the detector is adjusted or calibrated based upon this obtained fluorescence data. By adjusted or calibrated is meant that the sensitivity and/or resolution of the detector is altered depending on the obtained fluorescent data.

In addition to, or in place of the above described detector sensitivity calibration, one or more other optical components of the system are confirmed and/or calibrated or adjusted. For example, the focus position, dynamic focus and scanner mirror may be confirmed and/or adjusted, where such methods are described above.

In certain embodiments of the subject methods, the jitter of the optical scanner is verified or confirmed by scanning a pattern of photobleached regions or features, e.g., by scanning the photobleached regions of the above described calibration devices, where such methods are described above.

As mentioned above, an array is provided and a hybridization assay is performed to bind certain analytes or agents of interest, i.e., labeled analytes or agents (fluorescently labeled), to the array, or more specifically to certain polymeric binding agents or probes which make up an array.

The subject arrays include at least two distinct polymers that differ by monomeric sequence covalently attached to different and known locations on the substrate surface. Each distinct polymeric sequence of the array is typically present as a composition of multiple copies of the polymer on a substrate surface, e.g. as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm$^2$, where the density may be as high as $10^6$ or higher, but will generally not exceed about $10^5$ spots/cm$^2$.

In the broadest sense, the arrays of the subject invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. The biopolymeric arrays of the subject invention may be produced by a number of different methods, where such methods are known to those of skill in the art.

The arrays scanned according to subject methods find use in a variety applications, where such applications are generally analyte detection applications, as mentioned above, in which the presence of a particular analyte in a given sample is detected at least qualitatively, if not quantitatively. Protocols or hybridization techniques for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. fluorescent label present on the analyte, etc. The presence of the analyte in the sample is then deduced from the detection of binding complexes on the substrate surface.

Specifically, in hybridization assays, a sample of target nucleic acids or the like is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: WO 95/21265; WO 96/31622; WO 97/10365; WO 97/27317; EP 373 203; and EP 785 280; and U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

In gene expression analysis with microarrays, an array of "probe" nucleic acids is contacted with a nucleic acid sample of interest. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications.

Once the hybridization assay has been performed, the array is then interrogated, i.e., scanned, rastered or read by an optical means calibrated according to the subject invention, to detect, i.e., qualitate and/or quantify, labeled analyte or agent bound to the array. As such, the calibrated optical means (in other words at least one light source and a calibrated scanner) then scans or "reads" the hybridized array.

Thus, a biopolymeric array is exposed to a sample (for example, a fluorescently labeled polynucleotide or protein containing sample) and the array is then read using an apparatus calibrated according to the subject invention. Reading of the array may be accomplished by illuminating the array and reading the location and intensity of resulting fluorescence at each feature of the array. For example, a scanner, and more particularly a scanner calibrated according to the subject invention, may be used for this purpose which is similar to the GENEARRAY scanner available from Agilent Technologies, Palo Alto, Calif. Other suitable apparatus and methods are described in U.S. patent applications: Ser. No. 09/846125 "Reading Multi-Featured Arrays" by Dorsel et al.; and Ser. No. 09/430214 "Interrogating Multi-Featured Arrays" by Dorsel et al. These references are incorporated herein by reference.

More specifically, the hybridization array is placed in or on a calibrated optical scanner, i.e., is positioned in operative association with the calibrated optical means described above. Typically, a plurality of such hybridized arrays may be positioned in operative association with the calibrated optical means, for example a plurality may be indexed in an indexing means such as a carousel or the like, whereby each array is moved into a scanning position or is scanned by the optical means, followed by the scanning or reading of another array, i.e., an array positioned in an adjacent position in the indexing means to the previous scanned array. Regardless of the number of scanned arrays, an array is illuminated with at least one light source and the light emitted by each of the fluorescent labels thereon is detected by the calibrated detector. Specifically, a signal or voltage related to the presence and/or quantity of light emitted by the fluorescent labels is detected. Patents describing methods of optically detecting fluorescently labeled arrays include, but are not limited to: U.S. Pat. Nos. 5,631,734 and 5,981,956, the disclosures of which are herein incorporated by reference. Thus, it will be apparent that using the calibrated optical system to scan an array will result in more accurate and precise array scans.

Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

In certain embodiments, as mentioned above, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. The data may be transmitted to the remote location for further evaluation and/or use. Any convenient telecommunications means may be employed for transmitting the data, e.g., facsimile, modem, Internet, etc.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Kits

Finally, kits for use in calibrating optical scanners are provided. The subject kits at least include one or more calibration devices of the subject invention. Typically, a plurality of subject calibration devices is included. The kits may further include an optical scanner. The subject kits may also include one or more arrays. The kits may further include one or more additional components necessary for carrying out an analyte detection assay, such as sample preparation reagents, buffers, labels, and the like. As such, the kits may include one or more containers such as vials or bottles, with each container containing a separate component for the assay, such as an array, and reagents for carrying out nucleic acid hybridization assays according to the invention. Thus, the kit will comprise in packaged combination, an array, wherein the array comprises hybridization probes that selectively hybridize to the detectably labeled target nucleotide sequence, where such arrays may include background probes that do not selectively hybridize to the target nucleotide sequence. The kit may also include a denaturation reagent for denaturing the analyte, hybridization buffers, wash solutions, enzyme substrates, negative and positive controls and written instructions for carrying out the assay. Finally, the kits may further include instructions for using the subject devices for calibrating an optical scanner. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

EXAMPLES

The following example is put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following method describes an exemplary method of manufacturing the subject calibration devices.

I. Preparation of Stock Dye Solutions

Weigh out approximately 10(±2) mg of Green dye (for example Rhodamine 6G.HCl) and place in a clean, dry vial. Dissolve R6G in 10 ml ethanol and agitate on a shaker, stir plate or ultrasonic bath until solution is clear and all dye dissolved. Repeat the process using Red dye (for example HIDCI). Dilute the stock solutions in ethanol to a known absorbance, i.e., about 300 µL of prep solutions in 4.7 mL ethanol. Check the absorbances for these solutions to ensure they are about 0.161 @ 530 nm for R6G and about 0.278 @ 639 nm for HIDCI.

II. Preparation of Polymer Solution

Weigh out sufficient PMMA powder to produce a solution of about 1–20 wt % (depending on thickness of coating desired.) and place in a 100–150 ml glass bottle. Dissolve PMMA in 75 g of chlorobenzene by rotating jar overnight at 0.5 Hz (Cole-Parmer Roto-Torque cat. # E-07637-00). (If the solution is not clear and particle free, heat to 50° C. until it appears homogenous, and rotate for about 3 additional hours and allow to cool to room temperature.)

(Solution viscosity determines the final thickness of the spin coated test chip. Any changes in molecular weight or concentration affects the solution viscosity and necessitates revalidating the spin coating procedure.)

III. Preparation of Final PMMA/Dye Calibration Devices

Add 10 µL of prepared dye solution(s) to 100 ml of PMMA solution from above and stir on an orbital mixer for about 12–18 hours, allow any air bubbles to escape by letting the solution stand for 1 hour after removing from the stirrer (sonication or using reduced pressure can aid in degassing the solution if bubbles remain).

Clean substrates for coating and store in PTFE or similar wafer container. (Proceed with spin coating using outlined procedure to produce polymeric coatings of the desired thickness.)

IV. Spin Coating

Verify the vacuum and inert gas supply to the spin coating instrument.

Spin material onto glass wafers according to the following exemplary protocol: 1) one (1) second ramp-up to 500 rpm, 2) hold at 500 rpm for 10 seconds, 3) while holding at 500 rpm, pour PMMA/Dye solution for approximately 5–8 seconds, 4) three (3) second ramp to 1500 rpm, 5) hold at 1500 rpm for 60 seconds.

After spin program is finished, bake the calibration devices at about 60° C. for 60 seconds using contact mode on hot plate (or other suitable drying methods, as outlined above). Dice the devices or cut to a final size.

V. Results

The results of the above described process for spin coating calibration devices produce calibration devices have a polymer coating with two florescent agents therein and minimal local and global nonuniformities.

It is evident from the above results and discussions that the above described invention provides a simple and efficient way of aligning and calibrating an optical scanner and more particularly a biopolymeric array optical scanner. The above described invention provides for a number of advantages, including producing a stable output at the frequency or wavelength of interest, minimal local and global nonuniformities, ease of manufacture and ease of use. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A calibration device for confirming or calibrating a biopolymeric array optical scanner, said device comprising:
   (a) a polymer layer comprising at least one fluorescent agent; and
   (b) at least one region in said polymer layer absent said at least one fluorescent agent.

2. The calibration device according to claim 1, wherein said at least one region is photobleached.

3. The calibration device according to claim 1, wherein said device has minimal local and global nonuniformities.

4. The calibration device according to claim 3, wherein said global nonuniformity of said calibration device is less than about 5%.

5. The calibration device according to claim 3, wherein said local nonuniformity of said calibration device is less than about 5%.

6. The calibration device according to claim 1, wherein said polymer is selected from the group consisting of acrylates, epoxides, urethanes, polycarbonates, polyolefins, polyetherketones, polyesters, polystyrenes, polyethylstyrene, polysiloxanes, and copolymers thereof.

7. The calibration device according to claim 1, wherein said polymer is polymethyl-methacrylate.

8. The calibration device according to claim 1, wherein the thickness of said polymer layer ranges from about 0.25 micron to about 10 micron.

9. The calibration device according to claim 1, wherein the thickness of said polymer layer ranges from about 0.4 micron to about 1 micron.

10. The calibration device according to claim 1, wherein said device comprises a single polymer layer.

11. The calibration device according to claim 1, wherein said device comprises a plurality of polymer layers.

12. The calibration device according to claim 1, wherein said at least one fluorescent agent absorbs and emits light in the portion of the electromagnetic spectrum to which a photomultiplier tube of said optical scanner is sensitive.

13. The calibration device according to claim 1, wherein said at least one fluorescent agent absorbs and emits light in the wavelength range selected from the group consisting of ultraviolet, visible and infrared.

14. The calibration device according to claim 1, wherein said at least one fluorescent agent is distributed substantially uniformly throughout said polymer.

15. The calibration device according to claim 1, wherein said at least one fluorescent agent is present in said polymer in a final concentration ranging from about 1 ppm to about 5000 ppm.

16. The calibration device according to claim 1, wherein said device comprises at least two fluorescent agents.

17. The calibration device according to claim 1, wherein said polymer layer is selected from the group consisting of a spin-coated polymer layer, a draw coated polymer layer, a roller coated polymer layer, an electrodeposited polymer layer and a sprayed polymer layer.

18. A method for calibrating a biopolymeric array optical scanning system, said method comprising:
(a) illuminating a surface of a calibration device with at least one light source, wherein said calibration device is a calibration device according to claim 1;
(b) obtaining fluorescence data from said surface of said calibration device; and
(c) calibrating said optical scanning system based upon said fluorescence data.

19. The method according to claim 18, wherein said step of illuminating comprises illuminating said surface of said calibration device in the portion of the electromagnetic spectrum to which a photomultiplier tube of said optical scanner is sensitive.

20. The method according to claim 18, wherein said step of illuminating comprises illuminating said surface of said calibration device in the wavelength range selected from the group consisting of ultraviolet, visible and infrared.

21. The method according to claim 18, wherein said step of obtaining fluorescence data comprises detecting a signal related to the intensity of emitted light from said fluorescent agent.

22. The method according to claim 18, wherein said step of calibrating comprises calibrating the scale factor of said system.

23. The method of claim 22, wherein said scale factor calibration comprises adjusting the sensitivity of an optical detector of said system.

24. The method according to claim 18, wherein said step of calibrating comprises calibrating the focus position of said system.

25. The method according to claim 24, wherein said focus position calibration comprises adjusting the distance between a scanning stage and a lens of said system.

26. The method according to claim 18, wherein said step of calibrating comprises calibrating the dynamic focus of said system.

27. The method according to claim 26, wherein said dynamic focus calibration comprises adjusting the rate of speed at which an optical stage of said system travels.

28. The method according to claim 18, wherein said step of calibrating comprises determining the amount of oscillation in an intensity image and adjusting the rate of speed of said optical stage according to said oscillation data.

29. The method according to claim 18, wherein said step of calibrating comprises calibrating at least one scanner mirror of said system.

30. The method according to claim 29, wherein said at least one scanner mirror calibration comprises adjusting said at least one scanner mirror to synchronize the light beams of said system.

31. The method according to claim 18, further comprising the steps of subtracting a background signal from said obtained fluorescent data to obtain a background corrected value.

32. The method according to claim 18, wherein said fluorescent agent(s) is distributed substantially uniformly throughout said surface.

33. The method according to claim 18, further comprising the step of verifying the jitter of said optical scanning system.

34. A method for performing a hybridization assay, said method comprising:
(a) calibrating an optical scanner with a calibration device, wherein said calibration device is a calibration device according to claim 1,
(b) performing a hybridization assay with at least one array, and
(c) scanning said array with said calibrated optical scanner.

35. The method according to claim 34, wherein said method further comprises verifying the jitter of said optical scanner based on a scan of said photobleached area.

36. A method comprising forwarding data representing a result of a scan obtained by the method of claim 34.

37. The method according to claim 36, wherein said data is transmitted to a remote location.

38. A method comprising receiving data representing a result of an interrogation obtained by the method of claim 36.

39. A method for manufacturing a calibration device, said method comprising spin-coating a composition onto a substrate to produce a calibration device according to claim 1.

40. The method of claim 36, further comprising photobleaching at least one region of said device.

41. A kit for calibrating a biopolymeric array optical scanner, said kit comprising:
 (a) at least one device according to claim 1; and
 (b) a substrate comprising instruction for using said device to calibrate a biopolymeric array optical scanner.

42. A kit for calibrating a biopolymeric array optical scanner, said kit comprising:
 (a) at least one device according to claim 1; and
 (b) an array.

* * * * *